United States Patent [19]

Aldea

[11] Patent Number: 5,533,957
[45] Date of Patent: Jul. 9, 1996

[54] METHOD OF TISSUE RETROPERFUSION

[75] Inventor: Gabriel S. Aldea, Chestnut Hill, Mass.

[73] Assignee: Trustees of Boston University, Boston, Mass.

[21] Appl. No.: 444,049

[22] Filed: May 18, 1995

Related U.S. Application Data

[62] Division of Ser. No. 238,860, May 6, 1994.

[51] Int. Cl.⁶ .................................................. A61N 1/362
[52] U.S. Cl. .............................. 600/16; 128/898; 604/28; 604/53
[58] Field of Search .................................. 128/637, 898; 604/27, 28, 31, 53, 43, 45, 93, 118, 264; 600/16, 17

[56] References Cited

U.S. PATENT DOCUMENTS

| | | |
|---|---|---|
| 3,795,246 | 3/1974 | Sturgeon . |
| 3,833,003 | 9/1974 | Taricco . |
| 3,847,157 | 11/1974 | Caillouette et al. . |
| 4,180,068 | 12/1979 | Jacobsen et al. . |
| 4,459,977 | 7/1984 | Pizon .................................... 604/102 |
| 4,517,979 | 5/1985 | Pecenka . |
| 4,592,340 | 6/1986 | Boyles . |
| 4,601,706 | 7/1986 | Aillon . |
| 4,627,837 | 12/1986 | Gonzalo . |
| 4,689,041 | 8/1987 | Corday et al. . |
| 4,934,996 | 6/1990 | Mohl et al. . |
| 4,943,277 | 7/1990 | Bolling . |
| 4,969,470 | 11/1990 | Mohl et al. . |
| 5,024,668 | 6/1991 | Peters et al. . |
| 5,033,998 | 7/1991 | Corday et al. . |
| 5,037,398 | 8/1991 | Buchanan . |
| 5,312,344 | 5/1994 | Grinfeld ................................. 604/101 |
| 5,395,331 | 3/1995 | O'Neil ................................... 604/96 |
| 5,437,633 | 8/1995 | Manning ................................ 128/898 |
| 5,458,574 | 10/1995 | Machold ................................ 604/101 |

OTHER PUBLICATIONS

C. S. Beck, D. C. Leighringer, *Scientific Basis for The*

(List continued on next page.)

Primary Examiner—Randall L. Green
Assistant Examiner—Chalin Smith
Attorney, Agent, or Firm—Baker & Botts

[57] ABSTRACT

A catheter for retroperfusion of myocardium has an infusion tip, such that when retroperfusing myocardium, the tip extends within the coronary sinus to a depth in a range of about 2 to 4 inches (5 to 10 cm) from the coronary sinus ostium. The catheter also comprises a tube defining at least three channels. The channels include an infusion channel, which has a first infusion end coupled to an infusion port located in the infusion tip and a second infusion end coupled to an outlet orifice of a pump; a withdrawal channel, which has a first withdrawal end coupled to a withdrawal port located in the superior vena cava and a second withdrawal end coupled to an inlet orifice of the pump; and a pressure monitoring channel for monitoring pressure at pressure port at the infusion tip having a first end coupled to the pressure port and a second monitoring end coupled to a pressure sensor. The catheter also has a microprocessor for controlling the pump and measuring a rate of retroperfusate flow, whereby autologous venous blood entering the withdrawal port is continuously discharged at the infusion port at a flow rate in a range of about 5 to 50 mil./min. and at a pressure less than about 15 mm Hg. The tube and tip are made from biocompatible, non-thrombogenic material. Further, the catheter has remotely identifiable markers spaced along the tube, and a marker is located at said infusion tip. The invention also is a method for coronary sinus retroperfusion. The method includes the steps of inserting the catheter through the patient's jugular vein; guiding the catheter's infusion tip into the coronary sinus, such that when retroperfusing myocardium, the tip extends within the coronary sinus to a depth in a range of about 2 to 4 inches (5 to 10 cm) from the coronary sinus ostium; and providing a non-synchronized retroperfusate flow of autologous venous blood at a rate in a range of about 5 to 50 mil./min. and at a pressure less than about 15 mm Hg.

11 Claims, 7 Drawing Sheets

OTHER PUBLICATIONS

Surgical Treatment of Coronary Artery Disease, JAMA vol. 159: 1264 (1954).

M. T. Partington, C. Acar, G. D. Buckberg, et al.; *Studies of Retrograde Cardioplegia. I. Capillary Blood Flow Distribution to the Myocardium Supplied by Open and Occluded Arteries*, J. Thorac. Cardiovasc. Surg. 97:605–612 (1989).

M. T. Partington, C. Acar, G. D. Buckberg, et al.; *Studies of Retrograde Cardioplegia. II. Advantages of Antegrade/retrograde Cardioplegia to Optimize Distribution in Jeopardized Myocardium*, J. Thorac. Cardiovasc. Surg. 97: 613–622 (1989).

S. F. Bolling, J. T. Flaherty, B. H. Bulkley, et al.; *Improved Myocardial Preservation during Global Ischemia using Continuous Retrograde CS Perfusion*, J. Thorac. Cardiovasc. Surg. 86:659–666 (1983).

M. C. Stirling, T. B. McClanahan, K. P. Gallagher, et al.; *Distribution of Cardioplegic Solution Infused Antegradely and Retrogradely in Normal Canine Hearts*, J. Thorac. Cardiovasc. Surg. 98: 1066–1076 (1989).

P. Menasche, S. Kural, M. Fauchet, et al.; *Retrograde CS Perfusion: A Safe Alternative for Ensuring Cardioplegic Delivery in Aortic Valve Surgery*, Ann. Thorac. Surg. vol. 34, No. 6, 647–658 (1982).

P. Menasche, A. Piwnica; *Cardioplegia by Way of the Coronary Sinus for Valvular and Coronary Surgery*, J. Am. Coll. Cardiol. vol. 18, No. 2, 628–636 (1991).

H. L. Lazar, A. Rajaii, A. J. Roberts; *Reversal of Reperfusion Injury After Ischemic Arrest With Pressure–Controlled Intermittent Coronary Sinus Occulsion*, J. Thorac. Cardiovasc. Surg. 95:637–642 (1988).

H. L. Lazar, S. Rivers; *Improved Distribution of Cardioplegia With Pressure–Controlled Intermittent Coronary Sinus Occulsion*, Surg. Forum 38: 256–257 (1987).

H. L. Lazar; *Current Review: Coronary Sinus Interventions During Cardiac Surgery*, Ann. Thorac. Surg. 46: 475–482 (1988).

H. L. Lazar, G. D. Buckberg, A. Manganaro, et al.; *Myocardial Energy Replenishment and Reversal of Ischemic Damage by Substrate Enhancement of Secondary Blood Cardioplegia with Amino Acids During Reperfusion*, J. Thorac. Cardiovasc. Surg. 80: 350–359 (1980).

R. E. Austin, W. W. Hauck, G. S. Alden, J. I. E. Hoffman, et al.; *Quantitating Error in Blood Flow Measurements with Radioactive Microspheres*, Am. J. Physiol. (256) (Heart Circ. Physiol. 26) H280–H288 (1989).

G. S. Aldea, F. E. Austin, J. I. E. Hoffman, et al.; *Heterogenous Delivery of Cardioplegic Solution in the Absence of Coronary Artery Disease*, J. Thorac. Cardiovasc. Surg. vol. 99, No. 2, 345–353 (1990).

R. E. Austin, G. S. Aldea, J. I. E. Hoffman, et al.; *Profound Spatial Heterogeneity of Coronary Reserve*. Circulation Research vol. 67, No., 2 319–331 (1990).

D. L. Coggins, A. E. Flynn, R. E. Austin, G. S. Aldea, J. I. E. Hoffman; *Nonuniform Loss of Regional Flow Reserve during Myocardial Ischemia in Dogs*, Circulation Research vol. 67, No. 2, 253–264 (1990).

W. Mohl, D. H. Glogar, E. Wolner; *Reduction of Infarct Size Induced by Pressure–Controlled Intermittent Coronary Sinus Occlusion*, Am. J. Cardiol. 53: 923–928 (1984).

J. C. Farcot, S. Meerbaum, T. Lang, E. Corday, et al.; *Synchronized retroperfusion of coronary veins for circulatory support of jeopardized ischemic myocardium*, Am. J. Cardiol. 41: 1191–1201 (1976).

A. K. Jacobs; *Coronary Sinus Interventions: clinical application*, (W. Mohl, D. Faxon, E. Wolner (Eds.)), Steinkoff Darmstadt Springer–Verlag, 27–40 (New York 1986).

F. A. Fedele, R. J. Capone, A. S. Most, H. Gewirtz; *Effect of Pressure–Controlled Intermittent Coronary Sinus Occlusion on Pacing–Induced Myocardial Ischemia in Domestic Swine*, Circulation vol. 77, No. 6, 1403–1413 (1988).

M. V. Ludenghauser; *Nomenclature and Distribution Patterns of Cardiac Veins in Man* (Mohl W., Faxon D. (Eds.)), Clinics of Coronary Sinus Interventions, Proceedings of the 2nd International on Myocardial Protection via the Coronary Sinus, Steinkoff Darmstadt Springer–Verlag, 13–39 (New York 1986).

L. Ryden, H. Tadokoro, J. K. Drury, et al.; *Pharmacokinetic Analysis of Coronary Venous Retroinfusion: A Comparison of Anterograde Coronary Artery drug Administration using Metoproiol as a Tracer*, J. Am. Coll. Cardiol. vol. 18, No. 2, 603–612 (1991).

L. Berk, I. O. L. Schmeets, P. D. Verdouw, et al.; *On the Time Course of Systolic Myocardial Wall Thickening during Coronary Artery Occlusion and Reperfusion in the Absence of Synchronized Diastolic Coronary Venous Retroperfusion in Anesthetized Pigs*. Proceedings of the 2nd International Symposium on Myocardial Protection via the Coronary Sinus, Steinkof Darmstadt Springer–Verlag, 277–280 (New York 1986).

F. Beyersdorf, B. S. Allen, G. D. Buckberg, et al.; *Studies on Prolonged Acute Regional Ischemia*. J. Thorac. Cardiovasc. Surg. vol. 98, No. 1, 112–26 (1989).

J. Schafer, W. Shafer, *Reperfusion of Ischemic Myocardium; Ultrastructural and Histochemical Aspects*, J. Am. Coll. Cardiol. 4: 1037–1041 (1983).

H. L. Lazar, X. M. Yang, S. Rivers, et al.; *Role of Percutaneous Bypass in Reducing Infarot Size After Revascularization for Acute Coronary Insufficiency*, Circulation vol. 84, No. 5 (suppl. III), 416–421 (1991).

G. S. Aldea, G. Connelly, J. D. Fonger, et al.; *Directed Atraumatic Coronary Sinus Cannulation for Retrograde Cardioplegia Administration*, Ann. Thorac. Surf. 54: 789–90 (1992).

G. S. Aldea, D. Hou, J. D. Fonger, et al.; *Inhomogeneous and Complementary Antegrade and Retrograde Delivery of Cardioplegic Solution in the Absence of Coronary Artery Obstruction*, Forum Session–73rd Annual meeting of the American Association for Thoracic Surgery (Apr. 25–28 1993).

E. Y. Wakida, R. Nordlander, E. Corday, et al.; *Short–Term Synchronized Retroperfusion Reduces Infact Size after Prolonged Ischemia in Dogs*, Circulation 88: 2370–2380 (1993).

E. Y. Wakida, R. Nordlander, E. Corday, et al.; *Synchronized Coronary Venous Retroperfusion for Support and Salvage of Ischemic Myocardium During Elective and Failed Angioplasty*, J. Am. Coll. Cardiol. 18: 271–282 (1991).

K. J. Drury, Y. Shigeru, M. C. Fishbein, S. Meerbaum, E. Corday; *Synchronized Diastolic Coronary Venous Retroperfusion: Results Of A Preclinical Safety and Efficacy Study*, J. Am. Coll. Cardiol. 6: 328–335 (1985).

H. Lazar, T. Khoury, S. Rivers; *Improved Distribution of Cardioplegia With Pressure–Controlled Intermittent Coronary Sinus Occlusion,* Ann. Thorac. Surg. 46: 202–207 (1988).

J. Schaper, H. H. Scheld, U. Schmidt, F. Hehrlein; *Ultrastructural Study Comparing the Efficacy of Five Different Methods of Intraoperative Myocardial Protection in the Human Heart,* J. Thorac. Cardiovasc. Surg. 92: 47–55 (1986).

METHOD OF TISSUE RETROPERFUSION

This application is a division of application Ser. No. 08/238,860, filed May 6, 1994 pending.

BACKGROUND OF THE INVENTION

1. Field of the Invention

This invention relates to non-synchronized tissue retroperfusion at low flow rates and low pressures and more particularly, it relates to catheters for coronary sinus retroperfusion and methods of retroperfusion with such catheters.

2. Description of the Related Art

In the United States, over 1.5 million persons annually suffer from intractable ischemia or acute myocardial infarction, or both. Retroperfusion techniques for the heart generally involve the forceful delivery of arterial oxygenated or venous blood. This blood is delivered retrogradely to the endangered ischemic myocardium through its adjoining coronary veins in a direction opposite to the normal outflow of venous blood through that vein. Such retroperfused blood crosses from the coronary veins into the tissue capillary circulation, e.g., as microcirculation, to provide blood and nourishment to an underperfused myocardium.

Coronary sinus retroperfusion limits or reduces myocardial damage when administered as a preemptive or remedial treatment, or both. Coronary sinus retroperfusion also may be effective therapy when targeted to slow or, in some cases, reverse the progression from myocardial ischemia to the irreversible damage associated with myocardial infarction. Further, it may provide a temporary therapeutic window to achieve even more complete revascularization, such as by Percutaneous Transluminal Coronary Angioplasty (PTCA) or Coronary Artery By-Pass Grafting (CABG), and permits physicians to improve myocardial salvage.

A two-step surgical procedure involves creating a interventional shunt from the aorta (arterial blood) to the coronary sinus (venous circulation), and subsequently restricting the coronary sinus, such as with an occluding balloon, to facilitate effective retroperfusion of coronary veins with arterial blood. Nevertheless, this procedure may result in myocardial or vascular damage, or both. This damage may be attributed to the development of excessive congestion, edema, or hemorrhages resulting from interference with the coronary venous drainage and may cause permanent damage to the myocardium, which consequently may lead to infarction or death, or both. As a result of the difficulties encountered with such procedures and rising interest in surgical revascularization of coronary arteries as a means for treatment of coronary artery disease, research in coronary sinus retroperfusion slowed. Research involving surgical retroperfusion has explored the development of more regional coronary venous delivery of cardioplegic and other therapeutic solutions to particular zones of the heart, thus attempting to curtail potential myocardial damage due to poor coronary artery perfusion.

More recently, clinically oriented synchronized retroperfusion techniques have been used to reduce the hazards of myocardial edema mentioned above. Synchronized retroperfusion is achieved by the phasing of shunted arterial blood. Shunted arterial blood is pumped retrogradely into a coronary vein during diastole, while allowing coronary venous drainage in systole. The systolic pressure is the pressure exerted by the blood on the vessels, as a result of the force created by the contraction of the heart. This "time sharing" of the coronary veins permits a synchronized retroperfusion with unidirectional retrograde delivery of oxygenated blood into the ischemic area. Retrograde delivery is followed by normal coronary venous drainage. Such a method may support the acutely ischemic myocardium, restore its function, and reduce infarct size. The method also allows pharmacologic agents to be delivered along with oxygenated blood retroperfusion.

Coronary sinus retroperfusion methods, such as Synchronized Retroperfusion (SRP) or Pressure Controlled Intermittent Coronary Sinus Occlusion (PICSO), utilize high flow rates, such as flow rates in a range of about 100 to 250 mil./min. or pressure greater than about 30 mm Hg, or both. Such high flow rates also may result in large fluctuations in coronary sinus pressure. Large pressure fluctuations increase the risk of myocardial edema and damage from the coronary sinus intervention. In an attempt to reduce the risk of such damage, complicated gating and precise pressure monitoring are employed to control pressure fluctuations. Further, retroperfusion with arterial blood may involve at least two percutaneous catheter entries; a first entry in the artery from which blood is withdrawn and a second entry in the vein to which blood is infused. Thus, the use of coronary sinus retroperfusion generally has been limited to relatively small experimental, clinical trials because of concerns about the potential tissue damage which may be inflicted on patients if these techniques were widely used and less stringently controlled.

In synchronized retroperfusion, complex devices, such a pressure monitor devices, are attached to sensitive transducers and electronic monitoring devices capable of measuring, for example, arterial and pulmonary pressure to a high degree of accuracy. Such pressure monitor devices, however, may cause bubble formation within the artery. Such bubbles may eventually interfere with the pressure monitoring. In sophisticated pressure monitor devices, the bubbles are dislodged, and bubble gases vented. In order to effectively eliminate bubbles, it may be necessary to remove the pressure monitor device from the patient. Given the sensitivity of such devices, proper orientation is also significant. Pressure monitor devices are attached and reattached in a suitable position and level with the heart, so that movement of the device is limited in three axes.

Pressure monitor devices also are used in connection with a Swan-Gantz or pulmonary artery or arterial line catheters to assess the condition of patients in cardiovascular distress. Swan-Gantz catheters may be fed to a patient's pulmonary artery via the subclavian or jugular vein to directly monitor the pressure at one or more points. In order to obtain an accurate pressure reading, a balloon at the end of the catheter is inflated to block the artery and force back pressure, so that the catheter will only be exposed to the systolic pressure within the artery. Such pressure monitor devices may be connected to a transducer which converts the pressure signal to an electronic signal which may then be recorded on a chart monitor. A Swan-Gantz catheter and a pressure monitor device may be used, for example, to assess cardiovascular and pulmonary function, left ventricular function, and fluid status and cardiac output. These type of assessments generally are made on patients who suffer from cardiac conditions, such as left ventricle failure, cardiogenic shock, myocardial infraction (heart attack), hypovolemia (inadequate blood volume), and complex circulatory situations, such as acute burns.

Current retroperfusion catheters and retroperfusion methods present several disadvantages. The high flow rates or resultant high pressures, or both, may cause perforation and bleeding into the pericardium. PICSO and SRP occlude the coronary sinus and, therefore, raise coronary sinus pressure. For example, PICSO employs an inflatable balloon to occlude the coronary sinus, as described in U.S. Pat. No. 4,934,996 to Mohl et al. In addition to raising coronary sinus pressure by occluding the coronary sinus, SRP delivers an arterial blood flow at an increased force or flow rate. The risk of bleeding is high in SRP and PICSO methods and with surgical retroperfusion between a coronary artery and a coronary vein. Although bleeding is a danger in any tissue retroperfusion, bleeding in the pericardium is especially dangerous due to the risk of cardiac tamponade, i.e., compression of the heart's venous return due to increased volume of fluid in the pericardium. Further, because synchronized retroperfusion depends upon accurate pressure measurements to maintain safe retroperfusion, malfunctions in the pressure monitor device may cause coronary blood vessels to rupture or severe damage to the heart chambers. Moreover, the insertion of catheters at two entry points, e.g., an artery and a vein, in order to retroperfuse tissue with arterial, e.g., oxygenated, blood complicates retroperfusion and increases the invasiveness of the retroperfusion.

Such catheters are also cumbersome and may prove difficult to insert even for a trained cardiologist or cardiothoracic surgeon. The difficulty in inserting such catheters stems in part from the difficulty in accurately locating the catheter during insertion and precisely positioning the catheter's infusion port(s) within the coronary sinus, so that it does not slip out during retroperfusion. Further, because of the risk of myocardial damage caused by over-pressures, the retroperfusion flow is carefully monitored and controlled. However, as noted above, the complicated and expensive control monitor devices do not eliminate this risk. Moreover, in view of the severity of the risks involved, the very complexity of the control measures used in present retroperfusion processes may make such controls an unsuitable solution to the problems associated with high flow rate or overpressure, or both, in the general application of such methods.

SUMMARY OF THE INVENTION

Thus, a need has arisen for a safe and effective tissue retroperfusion catheter and a method for tissue retroperfusion which reduces the dangers of tissue damage caused by high flow rate and high pressures, e.g., high coronary sinus pressures, used in present catheters and retroperfusion methods. In particular, a need has arisen for a retroperfusion catheter and method which reduce the need for complicated pressure monitor devices and multiple points of entry to achieve retroperfusion. Thus, it is an advantage of this invention that the absence of repeated, intermittent venous obstruction, such as coronary sinus obstruction by an inflatable balloon in PICSO, reduces the risk of perforation of the vein and tissue damage, e.g., coronary sinus perforation and myocardial damage. A need has also arisen for a retroperfusion catheter and method which may retroperfuse tissue, such as myocardial tissue, with venous blood or a tissue enhancement solution, or both.

In an embodiment of this invention, a catheter is used for retroperfusion of tissue, such as an organ or a limb. The tissue has a defined systemic vein that drains blood from the tissue through a venous junction. The venous junction couples the vein to the greater circulatory system of the patient. The catheter comprises an infusion tip, such that when retroperfusing the tissue, the tip extends within the vein to a depth in a range of about 2 to 4 inches (5.08 to 10.16 cm) from the venous junction. The catheter also comprises a tube that defines a plurality of channels. The plurality of channels include at least one withdrawal channel, each of which has a first withdrawal end coupled to a withdrawal port and a second withdrawal end coupled to an inlet orifice of a pump; at least one infusion channel, each of which has a first infusion end coupled to an infusion port located in the infusion tip and a second infusion end coupled to an outlet orifice of the pump; and a pressure monitoring channel for monitoring pressure at a pressure port at the infusion tip having a first monitoring end coupled to the pressure port and a second monitoring end coupled to a pressure sensor. Further, the catheter comprises means for controlling the pump and measuring a rate of retroperfusate flow whereby fluid, such as an autologous sanguinous or an extrinsic asanguinous solution, entering the withdrawal port is discharged at the infusion port at a flow rate in a range of about 5 to 50 mil./min. and a pressure less than about 15 mm Hg. The tube and tip are made from biocompatible, non-thrombogenic material, such as a material having a coating of a heparin or hirudin bonding treatment on the surfaces of those components which come into contact with blood. Moreover, the catheter may comprise a plurality of remotely identifiable markers spaced along the tube, and at least one of these markers may be located at the infusion tip.

In another embodiment of the invention, a catheter for retroperfusion of myocardium comprises an infusion tip, such that when retroperfusing myocardium, the tip extends within the coronary sinus to a depth in a range of about 2 to 4 inches (5.08 to 10.16 cm) from the coronary sinus ostium. The catheter also comprises a tube defining a plurality of channels. The channels include at least one infusion channel, each of which has a first infusion end coupled to an infusion port located in the infusion tip and a second infusion end coupled to an outlet orifice of a pump; at least one withdrawal channel, each of which has a first withdrawal end coupled to a withdrawal port, e.g., located at a distance in a range of about 8 to 10 inches (20.32 to 25.4 cm) from the infusion port, and a second withdrawal end coupled to an inlet orifice of the pump; and a pressure monitoring channel for monitoring pressure at pressure port at the infusion tip having a first monitoring end coupled to the pressure port and a second monitoring end coupled to a pressure sensor. In addition, the catheter comprises means for controlling the pump and measuring a rate of retroperfusate flow, whereby fluid, such as an autologous sanguinous or an extrinsic asanguinous solution, entering the withdrawal port is discharged at the infusion port at a flow rate in a range of about 5 to 50 mil./min. and at a pressure less than about 15 mm Hg. As discussed above, the tube and tip are made from biocompatible, non-thrombogenic material. Further, the catheter may comprise a plurality of remotely identifiable markers spaced along the tube, and at least one of the markers may be located at said infusion tip.

Another embodiment of the invention is a method for retroperfusion of tissue having a defined systemic vein. The vein drains blood from the tissue through a venous junction which couples the vein to the greater circulatory system of the patient. The method comprises the steps of inserting a catheter having an infusion tip through a percutaneous venous entry; guiding the infusion tip into the vein, such that when retroperfusing the tissue, the tip extends within the vein to a depth in a range of about 2 to 4 inches (5.08 to 10.16 cm) from the venous junction; and providing a non-synchronized retroperfusate flow of fluid, such as an autologous sanguinous or an extrinsic asanguinous solution, at a flow rate in a range of about 5 to 50 mil./min. and at a pressure less than about 15 mm Hg.

In yet another embodiment, the invention comprises a method for coronary sinus retroperfusion. The method comprises the steps of inserting a catheter through a percutaneous venous entry, wherein the catheter includes an infusion tip; guiding the infusion tip into the coronary sinus, such that when retroperfusing myocardium, the tip extends within the coronary sinus to a depth in a range of about 2 to 4 inches (5.08 to 10.16 cm) from the coronary sinus ostium; and providing a non-synchronized retroperfusate flow of fluid, such as an autologous sanguinous or an extrinsic asanguinous solution, at a flow rate in a range of about 5 to 50 mil./min. and at a pressure less than about 15 mm Hg.

The present invention provides various technical advantages over known tissue, e.g., coronary sinus, retroperfusion catheters and retroperfusion methods. A technical advantage of this invention is that the non-synchronized retroperfusion at a low flow rate, such as a flow rate in the range of about 5 to 50 mil./min. may result in a greater than fifty percent reduction in the resultant myocardial infarction size of a standard infarct model. These results are comparable to those of more complex, gated retroperfusion strategies, such as PICSO and SRP. Another technical advantage is that the suitable infusion pumps, e.g., an intravenous withdrawal and infusion pump, are readily available in most hospital facilities. Because of the non-synchronous infusion, the low flow rate, and the resultant low pressure, the retroperfusion catheter and the method are safer than synchronous infusion devices utilizing greater flow rates and generating higher pressures, and this catheter may be simply inserted through a single percutaneous venous entry, it does not require cumbersome monitoring of high pressure retroperfusion catheters and methods. It is yet another technical advantage that the catheter may monitor intravascular pH and oximetry and may be used to analyze the effectiveness of the therapy as well as the severity of the patient's on-going myocardial ischemia.

Still another technical advantage is that pharmaceutical agents may be delivered to the coronary sinus, selectively in the area at risk beyond a myocardial artery obstruction while sparing adjacent "normal" myocardium. Further, because the tube may include a plurality of pharmaceutical agent delivery channels, a plurality of pharmaceutical agents may be delivered at different flow rates. Moreover, separate channels permit pharmaceutical agents which are incompatible, e.g., which crystalize, when combined outside of a patient's bloodstream to be delivered to the patient via the catheter. Because the pharmaceutical agents are selectively delivered and, therefore, may be utilized in much lower doses, the risk and cost of such interventions are reduced. Such therapies had previously been unavailable to many patients because of the potential side effects of the intravenous doses of pharmaceutical agents. The present invention makes tissue retroperfusion, such as coronary sinus retroperfusion, more widely available because the therapeutic intracoronary dose delivered through the coronary sinus is significantly lower, e.g., as little as a tenth, of the intravenous dose, and the lower flow rates and pressures place less stress on the patient.

Other technical advantages are readily apparent to one skilled in the art from the drawings, descriptions, and claims.

BRIEF DESCRIPTION OF THE DRAWINGS

For a more complete understanding of the present invention and technical advantages thereof, reference is made to the following description taken in conjunction with accompanying drawings in which.

DETAILED DESCRIPTION OF THE INVENTION

Figure 1:
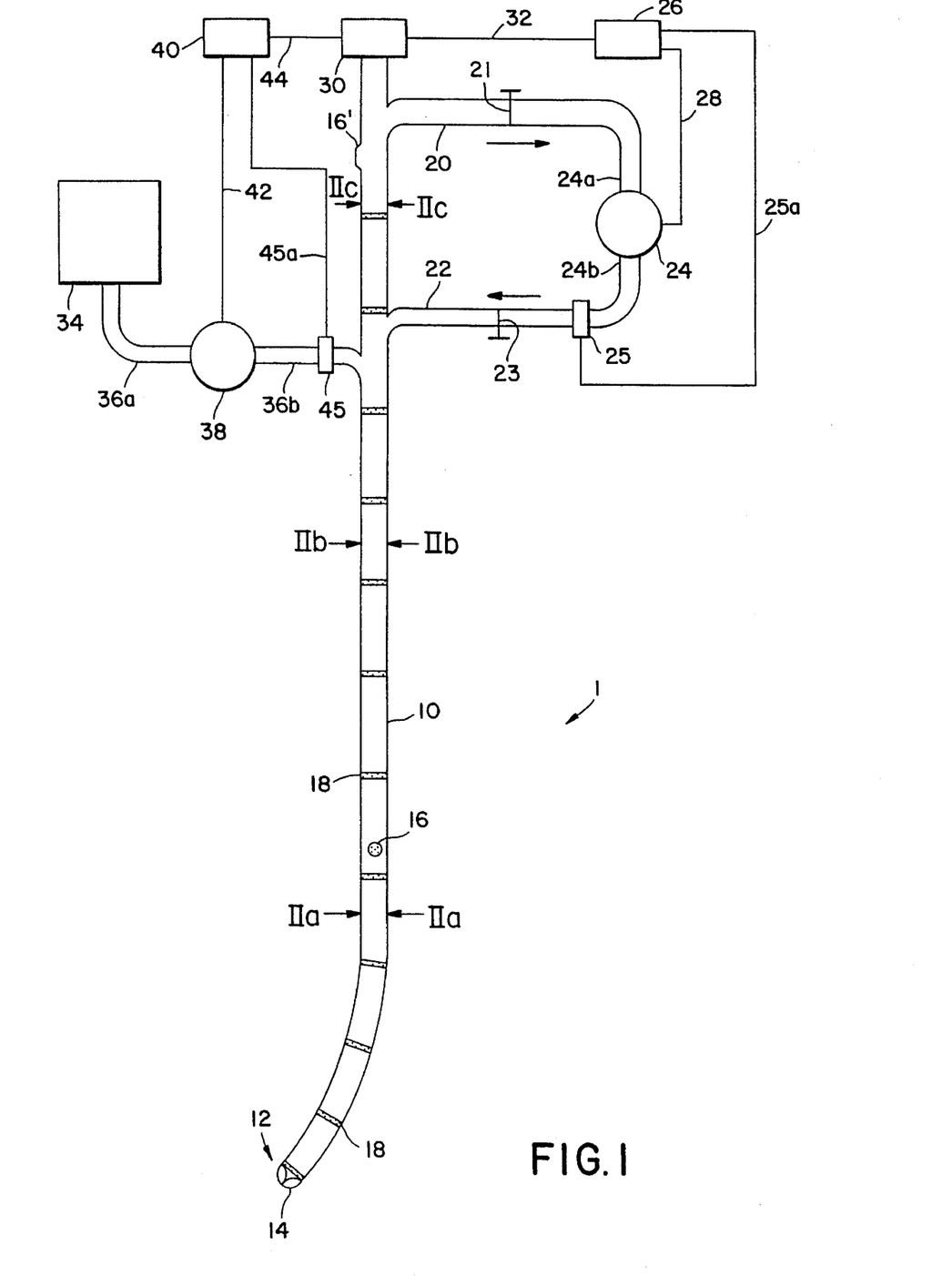
FIG. 1 is a schematic diagram of an embodiment of a coronary sinus retroperfusion catheter according to the invention.

Referring to FIG. 1, a catheter 1 includes a tube 10 and an infusion tip 12. Infusion tip 12 has three infusion ports 14 (only two shown). A retroperfusate flow of fluid, such as an autologous sanguinous or an extrinsic asanguinous solution, flows through one of these infusion ports. The other infusion ports are used to deliver a pharmaceutical agent or agents to the ischemic area, and a pressure port (not shown) is used to monitor blood pressure at infusion tip 12. Catheter 1 also includes a withdrawal port 16 (or alternate withdrawal port 16' for retroperfusion with, for example, extrinsic solution) and remotely identifiable markers 18. Remotely identifiable markers 18 are spaced periodically along tube 10 at intervals of about 2 inches (5.08 cm), and one of markers 18 is located at infusion tip 12. Thus, withdrawal port 16 is located about 8 to 10 inches (20.32 to 25.4 cm) from infusion tip 12 and infusion ports 14. Markers 18 are used to locate and position catheter 1 within a patient. For example, markers 18 may be fluoroscopically opaque and detectable with a fluoroscope (not shown). Alternatively, markers 18 may have echocardiographically distinct signatures and may be detectable on an echocardiograph (not shown).

Catheter 1 further includes a withdrawal channel 20 extending within tube 10 between withdrawal port 16 (or alternative withdrawal port 16') and an inlet 24a of a pump 24 and an infusion channel 22 extending within tube 10 between one of infusion ports 14 and an outlet 24b of pump 24. Pump 24 may be a standard intravenous infusion pump using an external power source (not shown) and commonly found in hospitals and clinics. Alternatively, pump 24 may employ a pump micromotor (not shown) and associated portable energy source (not shown) and be housed within tube 10. Withdrawal channel 20 and infusion channel 22 are equipped with venting connections 21 and 23, respectively. Connections 21 and 23 are used to vent gases from channels 20 and 22 to prevent damage to pump 24 and infusion of gases into the patient. Moreover, connections 21 and 23 permit rapid replacement of pump 24 in the event of pump failure.

A pressure sensor 30 is coupled to one end of a pressure monitoring channel (not shown) which extends within tube 10 between sensor 30 and a pressure port (not shown) in infusion tip 12. The pressure monitoring channel may contain a pressure transducer (not shown) which converts the blood pressure detected at infusion tip 12 into an output signal at sensor 30. If the pressure detected at infusion tip 12 equals or exceeds a safety pressure limit, such as about 15 mm Hg, sensor 30 sends a signal to means 26 for controlling pump 24 via a sensor-control means line 32, and means 26 for controlling pump 24 sends a signal to pump 24 via control means-pump line 28 to reduce (or cease) output from pump 24. Means 26 may comprise a processor (not shown), such as microprocessor, for analyzing signals received from sensor 30 and a transducer for converting signals from sensor 30 to electric or electromechanical signals for reducing (or ceasing) output from pump 24. Means for controlling intravenous infusion pumps are known. In addition, sensor 30 may detect low blood pressure in the ischemic area which may indicate failure of catheter 1 (or pump 24), such as, for example, a blockage in withdrawal channel 20 or infusion channel 22.

Because the pump 24 may be a metering pump, output or flow rate as well as output pressure from pump 24 may be controlled by varying speed of pump 24. Additionally, infusion channel 22 may be equipped with a flowmeter 25, such as a propeller-type flowmeter, ultrasonic flowmeter, mass flowmeter, and the like. A feedback loop 25a may also be used to adjust pump speeds and thereby adjust flow rates, e.g., within a range of about 5 to 50 mil./min.

Catheter 1 may also include a reservoir 34 containing a pharmaceutical agent or agents. A pharmaceutical agent delivery channel 36a–b may extend between reservoir 34 and one of infusion ports 14 at infusion tip 12. Alternatively, pharmaceutical infusion ports (not shown) may be located at other points along tube 10. A delivery means 38, such as a metering pump, is used to provide a measured flow of the pharmaceutical agent or agents from reservoir 34 to the patient. The flow of pharmaceutical agent or agents is controlled by a regulator 40. Regulator 40 may include a processor (not shown), such as a microprocessor, and a transducer (not shown) for controlling delivery means 38 via regulator-delivery means line 42. Regulator 40 may be programmable, so that various pharmaceutical agents or combinations of pharmaceutical agents may be identified and various flow rates for the agents or combinations of agents selected.

Regulator 40 also receives signals from sensor 30 via sensor-regulator line 44, so that the flow rate of pharmaceutical agent(s) may be reduced (or ceased) if the pressure detected at infusion tip 12 equals or exceeds a safety pressure limit, such as about 15 mm Hg. Further, pharmaceutical agent delivery channel 36a–b may be equipped with a flowmeter 45, such as a propeller-type flowmeter, ultrasonic flowmeter, mass flowmeter, and the like. A feedback loop 45a may also be used to adjust delivery means' speed and thereby adjust flow rates within a range selected for the pharmaceutical agent or combination of agents and the patient's condition.

Figure 2A:
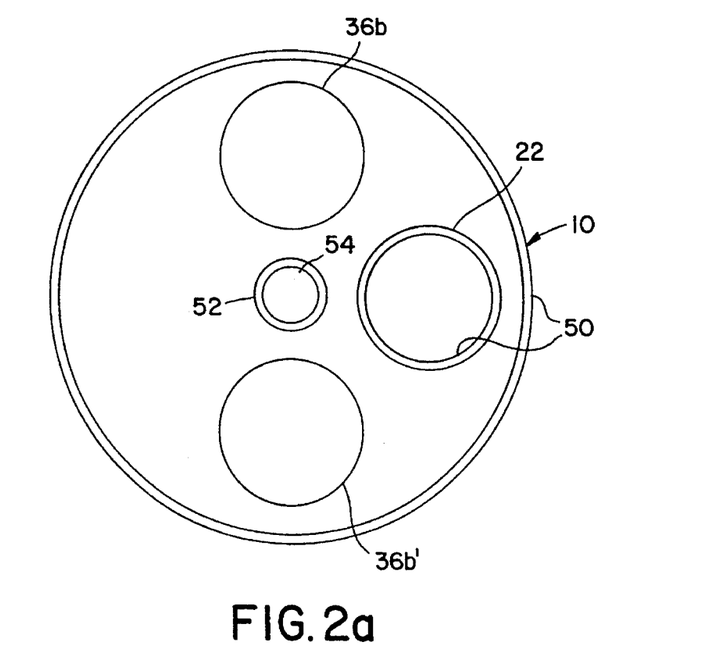
FIG. 2a depicts a cross-sectional view of an embodiment of the catheter of FIG. 1, along line of IIa—IIa.
Figure 2B:
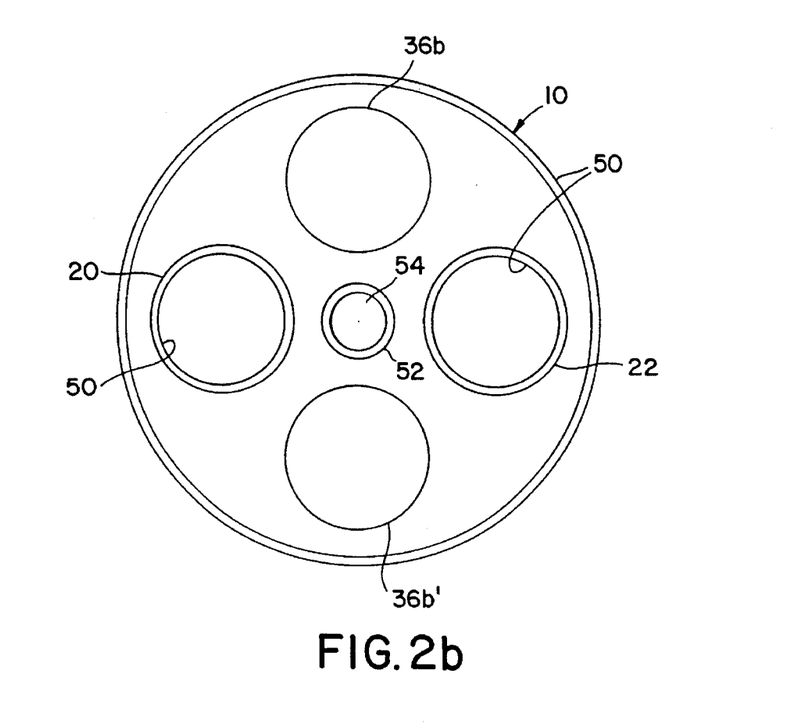
FIG. 2b depicts a cross-sectional view of an embodiment of the catheter of FIG. 1, along line IIb—IIb.
Figure 2C:
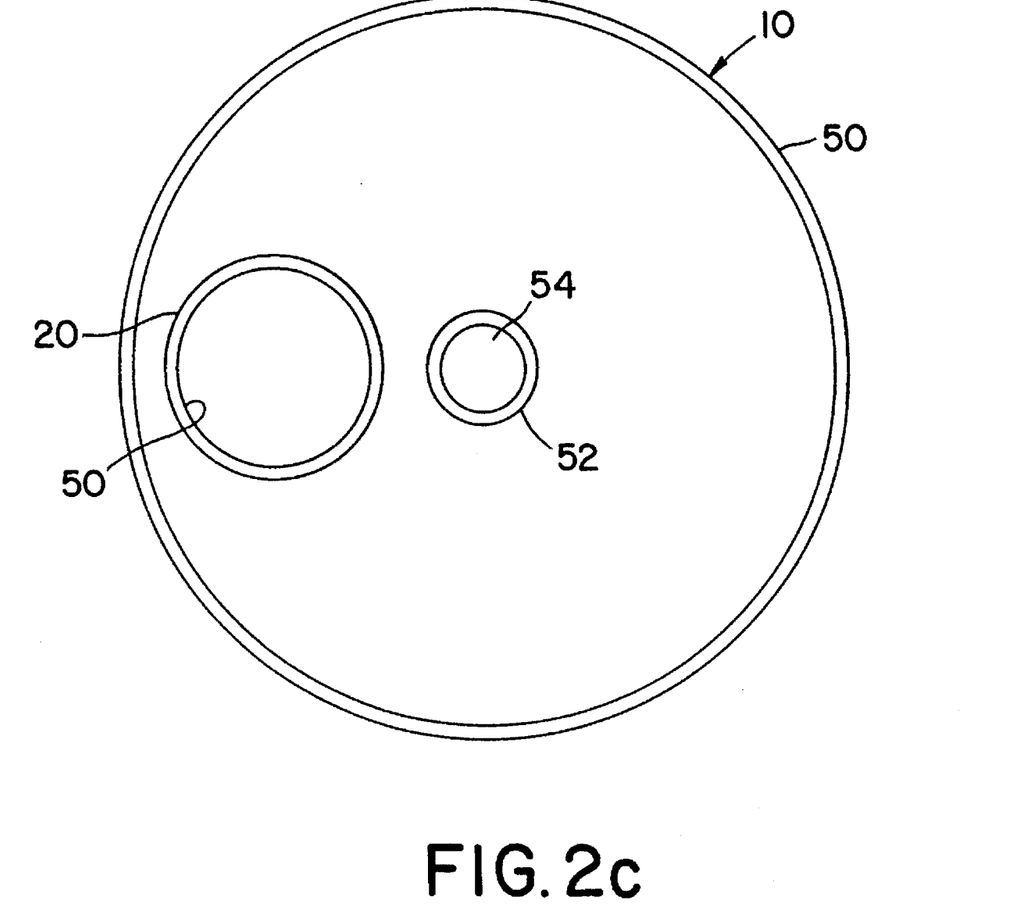
FIG. 2c depicts a cross-sectional view of an embodiment of the catheter of FIG. 1, along line IIc—IIc.

FIG. 2a depicts a cross-sectional view of an embodiment of the catheter of FIG. 1, along line IIa—IIa; FIG. 2b depicts a cross-sectional view of an embodiment of the catheter of FIG. 1, along line IIb—IIb; and FIG. 2c depicts a cross-sectional view of an embodiment of the catheter of FIG. 1, along IIc—IIc. Tube 10 is made from a biocompatible, non-thrombogenic material. For example, referring to FIGS. 2a–c, tube 10 has a heparin bonding treatment 50. This treatment 50 also lines withdrawal channel 20 and infusion channel 22. Withdrawal and infusion channels 20 and 22, respectively, may have inner diameters in a range of about 0.04 to 0.08 inches (1.02 to 2.04 mm), and tube 10 may have an outer diameter in a range of about 0.16 to 0.21 inches (4.06 to 5.33 mm). Treatment 50 reduces coagulation in sanguinous solutions at flow rates in the range of about 5 to 50 mil./min. Two pharmaceutical agent delivery channels 36b and 36b'are also depicted in FIGS. 2a and 2b. Separate channels increase the flexibility of the catheter in delivering pharmaceutical agents. Agents may be delivered at different agent infusion ports or at different rates. Moreover, agents which are incompatible with each other outside of the blood stream, e.g., which crystallize when combined, may be delivered with a single catheter.

FIGS. 2a–c also show a pressure monitoring channel 52. Channel 52 may contain a removable transducer 54 which extends between infusion tip 12 and sensor 30. Transducer 54 may be replaced with a known steering wire (not shown), such as steerable guide wires having a diameter of about 0.014 inches (0.36 mm), manufactured by USCI Company of Billerica, Mass., U.S.A., when inserting the catheter into a patient and guiding the catheter within the patient.

The catheters depicted in FIGS. 1 and 2a–c may be used to retroperfuse ischemic tissue, especially ischemic myocardium. Catheter 1 shows withdrawal port 16 located, so that venous blood may be withdrawn from the patient and retroperfused to supply blood flow to an ischemic area, e.g., an area to which arterial blood flow is blocked. Blockage may be caused by clogging of the arteries or injury, such as acute burns to limbs. Retroperfusion may employ an autologous sanguinous solution, such as venous or arterial blood or a solution including blood, or an extrinsic asanguinous solution, such as artificial serum, an oxygenated or non-oxygenated crystalloid plasmatic solution, a solution including aspartate or glutamate, or other tissue enhancement solution. Suitable tissue enhancing solutions have a normal pH of about 7.4 and an oncotic pressure approximately equal to that of blood and may contain buffers, e.g., bicarbonate, to modify the acidity present in the ischemic tissue and membrane stabilizing additives, such as lidocaine or magnesium. Such solutions may reduce harm to endothelia and may speed recovery after more complete revascularization, such as by PTCA or CABG, and thereby permit physicians to maximize myocardial salvage.

Figure 3:
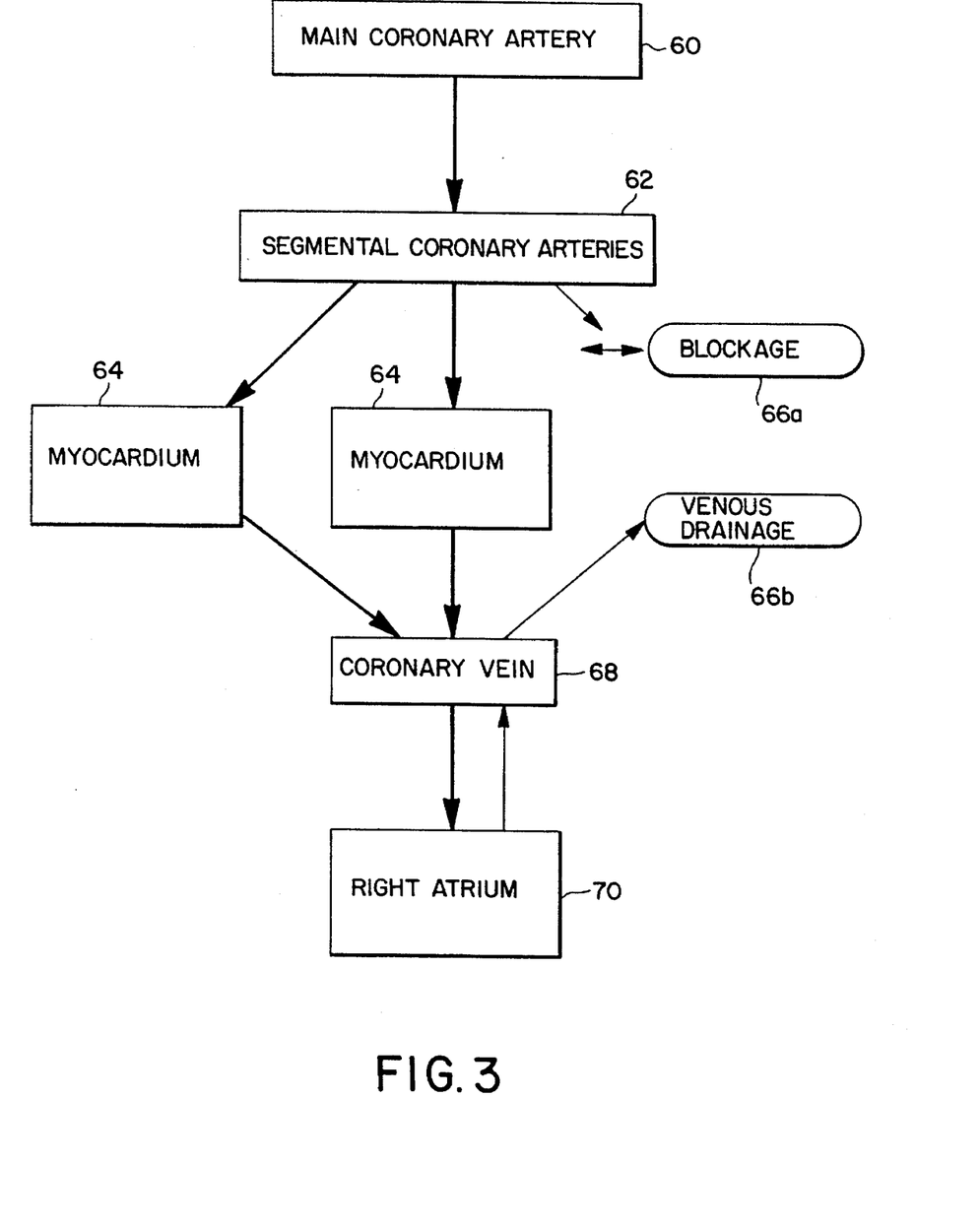
FIG. 3 is a flow diagram depicting the regional flow pathways with coronary sinus retroperfusion.

Referring to FIG. 3, the regional flow pathways for coronary sinus retroperfusion are depicted. Oxygenated blood for heart function is supplied via the main coronary artery 60. Main coronary artery 60 supplies oxygenated blood to segmented coronary arteries 62 which provide the blood supply to myocardium 64, i.e., heart tissue, unless a blockage 66a prevents the oxygenated blood from reaching the myocardium, i.e., in an ischemic area. Blood is drained from myocardium 64 by coronary veins 68 via the coronary sinus to the right atrium 70. Infusion tip 12 of catheter 1 described above may be inserted into the coronary sinus and positioned, so that venous blood from the right atrium 70 (or from the superior vena cava (not shown) which drains blood from the upper portions of the patient's body to the right atrium 70) is retroperfused via coronary vein 68 to the venous drainage 66b for the blocked myocardium, i.e., the ischemic area.

Figure 4:
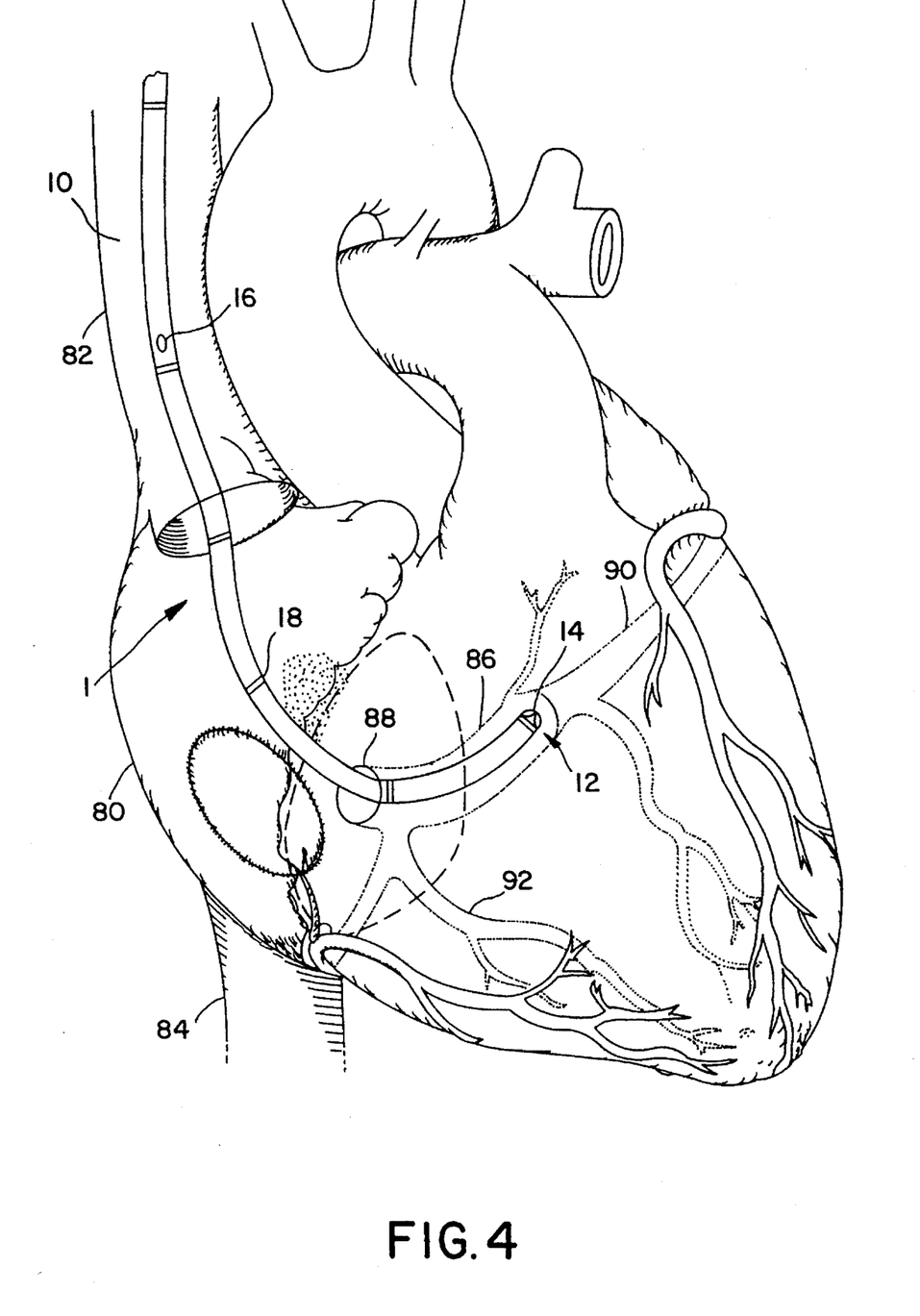
FIG. 4 depicts the placement of the catheter of FIG. 1 in the coronary sinus.

FIG. 4 depicts catheter 1 positioned within a patient's heart. Catheter 1 is inserted through a percutaneous venous entry, such as through the jugular vein, and infusion tip 12 is guided through the right atrium 80 into the coronary sinus 86. Blood drains to the right atrium 80 via the superior vena cava 82 and the inferior vena cava 84 and from the coronary sinus 86 via the coronary sinus ostium 88. Moreover, blood drains from the myocardium to the coronary sinus 86 via the large coronary vein 90 and the small coronary vein 92.

Infusion tip 12 having infusion ports 14 is inserted into the coronary sinus 86 to a depth of about 2 to 4 inches (5.08 to 10.16 cm) from the coronary sinus ostium 88. Insertion to this depth helps prevent infusion tip 12 from slipping from the coronary sinus 86 into the right atrium 80. Depending on the size of the patient's heart, withdrawal port 16 may be located in a range of about 8 to 10 inches (20.32 to 25.4 cm) from infusion tip 12. This distance allows withdrawal port 16 to be positioned in the superior vena cava 82. Because markers 18 are spaced about 2 inches (5.08 cm) apart along tube 10 and one markers 18 is at infusion tip 12, catheter 1 may be positioned accurately within the patient. Thus, as shown in FIG. catheter 1 may be used to proved continuous retroperfusion of autologous venous blood.

Figure 5:
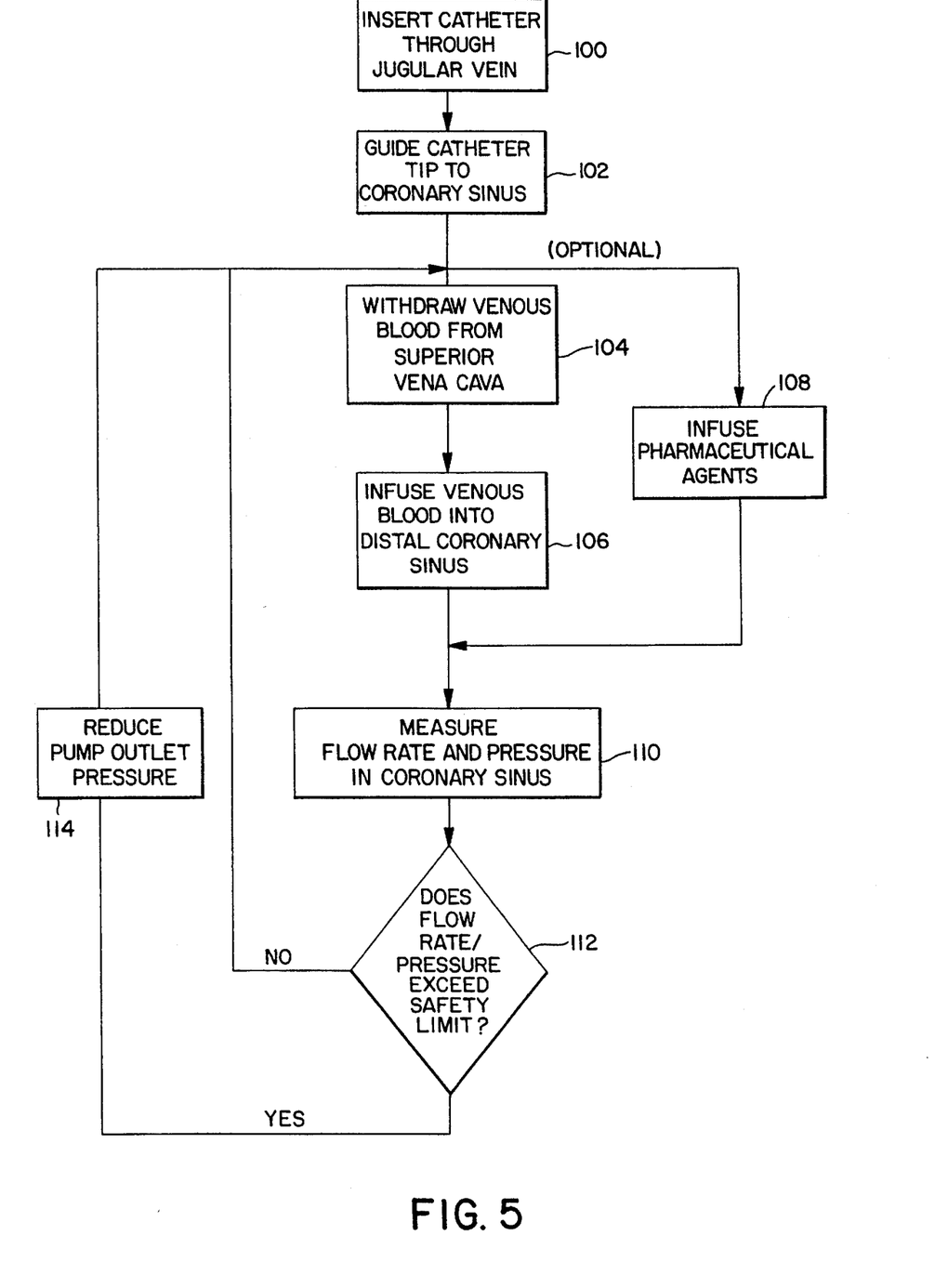
FIG. 5 is a flow chart showing a retroperfusion method according to the invention.

Referring to FIG. 5, a flow chart depicts a coronary sinus retroperfusion method according to this invention. As mentioned above, catheter 1 may be inserted through a single percutaneous venous entry, such as through the jugular vein, as indicated in step 100. In step 102, infusion tip 12 of catheter 1 is then guided to the coronary sinus 86. As discussed above, transducer 54 may be removed from pressure monitoring channel 52 and a guide wire may be inserted into channel 54 to guide catheter 1 within the patient's body. Further, because markers 18 are remotely identifiable, for example, with a fluoroscope, an echocardiograph, or the like, infusion tip 12 and withdrawal port 16 may be accurately positioned within the patient. Moreover, the separation between infusion tip 12 and withdrawal port 16 may be selected to place withdrawal port 16 in the superior vena cava 82 of most patients.

Once catheter 1 is in position, venous blood is withdrawn through withdrawal port 16 from the superior vena cava 82 in step 104. The withdrawn venous blood is then infused into the distal coronary sinus, i.e., the portion of the coronary sinus 86 at a distance in a range of about 2 to 4 inches (5.08 to 10.16 cm) from the coronary sinus ostium 88, as indicated in step 106. While the retroperfusion of steps 104 and 106 is occurring, pharmaceutical agents may also be infused from infusion tip 12 or other infusion ports located along tube 10 according to step 108.

Retroperfusion is non-synchronous, i.e., continuous, and the infusion flow rate and blood pressure are monitored in the coronary sinus 86. According to step 112, if the flow rate and the resultant blood pressure do not exceed the safety pressure limit, the retroperfusion continues. However, if the blood pressure exceeds the safety limit, pump outlet pressure (and consequently retroperfusion flow rate) is reduced in step 114.

Figure 6:
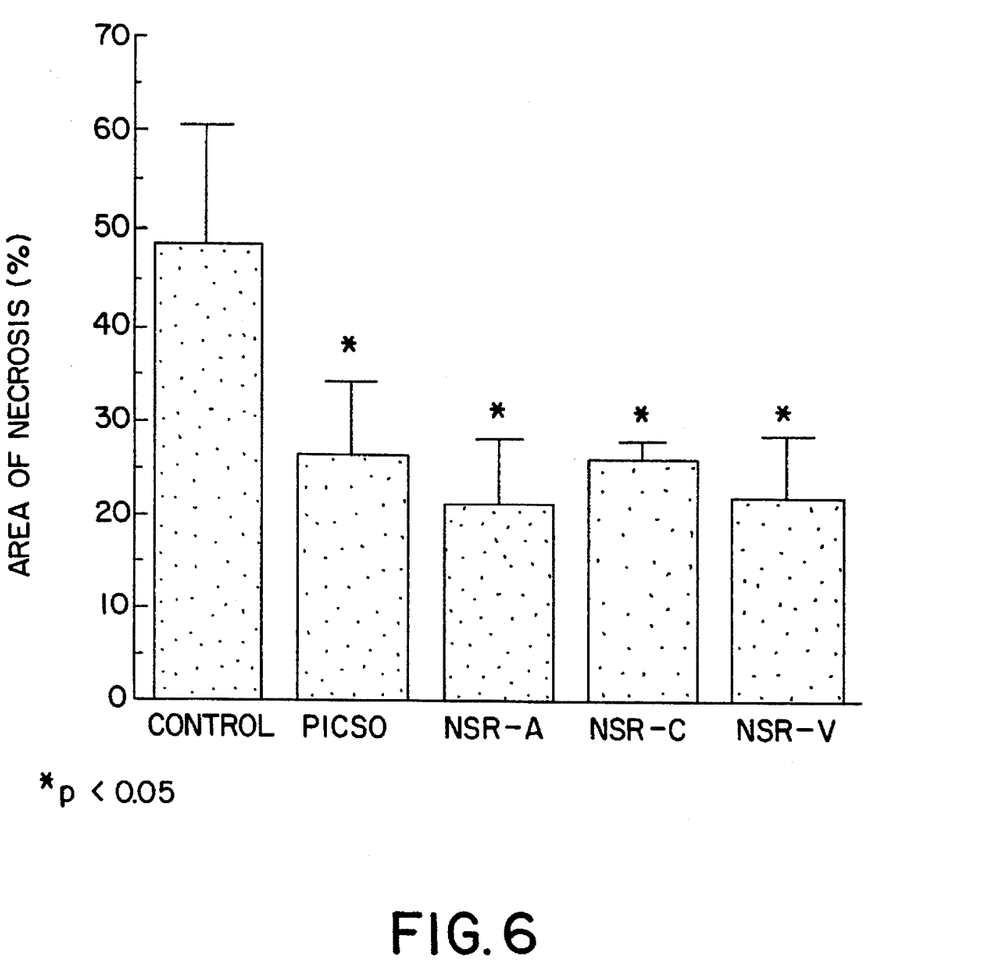
FIG. 6 is a bar graph showing a comparison of experimental results of different retroperfusion strategies.

FIG. 6 depicts the results of comparisons of various retroperfusion strategies based on experimentation performed on twenty-eight yorkshire pigs. The pigs were divided into five groups. Each group contained six pigs except NSR-V, which contained four pigs and represents non-synchronized venous retroperfusion using a catheter and method according to this invention. Each of the pigs was anesthetized, and a coronary artery was blocked to impose myocardial ischemia. For about sixty minutes following imposition of ischemia, the control group of six pigs received no intervention. The remaining pigs were treated with PICSO (gated) retroperfusion, non-synchronized retroperfusion with arterial blood (NSR-A), non-synchronized retroperfusion with crystalloid plasmatic solution (NSR-C), and non-synchronized retroperfusion with venous blood (NSR-V). After about forty-five minutes, the coronary artery occlusion was released simulating coronary revascularization, retroperfusion continued for about fifteen minutes, and then all of the pigs were reperfused for about three hours. After reperfusion, the pigs were euthanized, and samples were taken to determine the percentage of necrosis in the ischemic tissue.

Referring to FIG. 6, the percentage of necrosis found in the NSR-A and NSR-V groups was about one-half the percentage of the control group and lower than that obtained from the PICSO group. Further, although the PICSO group experienced a percentage of necrosis similar to the NSR-C group, each of the NSR groups was exposed to lower blood pressures during retroperfusion. The results depicted in FIG. 6, however, are intended to be purely exemplary of the use of the invention.

Although a detailed description of the present invention has been provided above, it is to be understood that the scope of the invention is to be determined by the claims that follow. Although coronary sinus retroperfusion was described in detail, these catheters and methods may be modified for preservation of other biological organs during active ischemia, as clinically indicated.

I claim:

1. A method for retroperfusion of tissue having a defined systemic vein, said vein draining blood from said tissue through a venous junction coupling said vein to the greater circulatory system comprising the steps of:

inserting a non-occluding catheter having a non-occluding infusion tip through a percutaneous venous entry;

guiding said infusion tip into said vein, such that when retroperfusing the tissue, said tip extends within said vein to a depth in a range of about 2 to 4 inches (5.08 to 10.16 cm) from said venous junction; and retroperfusing the tissue by delivering a non-synchronized retroperfusate flow of fluid at a rate in a range of about 5 to 50 mil./min. and at a pressure less than about 15 mm Hg.

2. A method for coronary sinus retroperfusion, comprising the steps of:

inserting a non-occluding catheter through a percutaneous venous entry, wherein said catheter includes a non-occluding infusion tip;

guiding said infusion tip into the coronary sinus, such that when retroperfusing myocardium, said tip extends within the coronary sinus to a depth in a range of about 2 to 4 inches (5.08 to 10.16 cm) from the coronary sinus ostium; and does not occlude the coronary sinus, such that said blood continues to flow from the coronary sinus and retroperfusing the myocardium by delivering a non-synchronized retroperfusate flow of fluid at a rate in a range of about 5 to 50 mil./min. and at a pressure less than about 15 mm Hg.

3. The method of claim 2, wherein said venous entry is an internal stick through the jugular vein.

4. The method of claim 2, wherein said catheter has a withdrawal port and further comprising the step of positioning said withdrawal port in the superior vena cava and wherein said step of providing said retroperfusate flow of fluid comprises withdrawing venous blood from the superior vena cava and infusing said venous blood into the coronary sinus.

5. The method of claim 2, further comprising the steps of:

measuring blood pressure within said coronary sinus;

comparing said measured blood pressure to a safety pressure limit; and reducing said retroperfusate flow rate when said measured blood pressure exceeds said safety pressure limit.

6. The method of claim 2, further comprising fitting said catheter with a catheter steering wire and guiding said infusion tip into the coronary sinus.

7. The method of claim 2, wherein said catheter has a catheter tube having a plurality of depth markers and said step of guiding said catheter further comprises a process selected from the group consisting of observing fluoroscopically opaque depth markers on a catheter tube and locating depth markers having echocardiographic signatures to locate and monitor the position of said catheter.

8. The method of claim 2, further comprising the step of selecting said fluid to be an autologous sanguinous solution.

9. The method of claim 2, further comprising the step of selecting said fluid to include an extrinsic sanguinous solution.

10. The method of claim 2, wherein said catheter further comprises at least one reservoir containing a pharmaceutical agent, and further comprising the step of infusing pharmaceutical agents into the coronary sinus wherein said catheter further comprises a tube defining at least one pharmaceutical agent delivery channel, each of which has a delivery end coupled to an agent infusion port located in said infusion tip and a source end coupled to a delivery means for providing a measured flow of said pharmaceutical agent from said reservoir.

11. The method of claim 2, wherein said retroperfusate flow is delivered at a rate of about 10 mil./min.

* * * * *